United States Patent
Saitoh et al.

(10) Patent No.: US 11,806,153 B2
(45) Date of Patent: Nov. 7, 2023

(54) PORTABLE ELECTROCARDIOGRAPH AND ELECTROCARDIOGRAPHY SYSTEM

(71) Applicant: NIHON KOHDEN CORPORATION, Tokyo (JP)

(72) Inventors: Satoshi Saitoh, Tokorozawa (JP); Jun Motogi, Tokorozawa (JP)

(73) Assignee: NIHON KOHDEN CORPORATION, Tokyo (JP)

(*) Notice: Subject to any disclaimer, the term of this patent is extended or adjusted under 35 U.S.C. 154(b) by 352 days.

(21) Appl. No.: 16/958,366

(22) PCT Filed: Jan. 24, 2019

(86) PCT No.: PCT/JP2019/002282
§ 371 (c)(1),
(2) Date: Jun. 26, 2020

(87) PCT Pub. No.: WO2019/151103
PCT Pub. Date: Aug. 8, 2019

(65) Prior Publication Data
US 2021/0085201 A1    Mar. 25, 2021

(30) Foreign Application Priority Data

Feb. 2, 2018   (JP) .................. 2018-017136
Oct. 5, 2018   (JP) .................. 2018-189957

(51) Int. Cl.
*A61B 5/332*   (2021.01)
*A61B 5/00*    (2006.01)
(Continued)

(52) U.S. Cl.
CPC ............ *A61B 5/332* (2021.01); *A61B 5/0006* (2013.01); *A61B 5/316* (2021.01); *A61B 5/335* (2021.01);
(Continued)

(58) Field of Classification Search
None
See application file for complete search history.

(56) References Cited

U.S. PATENT DOCUMENTS 11,471,107 B2 * 10/2022 Chang ................ A61B 5/339
2005/0141591 A1   6/2005 Sakano
(Continued)

FOREIGN PATENT DOCUMENTS

EP   3560422 A1 * 10/2019 ......... A61B 5/0006
JP   H08-299293 A   11/1996
(Continued)

OTHER PUBLICATIONS

Japanese Office Action dated Aug. 9, 2022 issued in Japanese Patent Application No. 2018-189957.
(Continued)

*Primary Examiner* — Kennedy Schaetzle
(74) *Attorney, Agent, or Firm* — Pearne & Gordon, LLP (57) ABSTRACT

A portable electrocardiograph includes: a recording section configured to record data corresponding to electrocardiogram of a subject; a detecting section configured to detect approach of a portable device having a function to perform short-range wireless communication; and a control section configured to start recording of the data in the recording section in a case where it is satisfied a start condition including a fact that the approach of the device is detected by the detecting section.

15 Claims, 5 Drawing Sheets

(51) Int. Cl.
  *A61B 5/316* (2021.01)
  *A61B 5/335* (2021.01)
  *A61B 5/364* (2021.01)

(52) U.S. Cl.
  CPC ...... *A61B 5/364* (2021.01); *A61B 2560/0214* (2013.01)

(56) References Cited

U.S. PATENT DOCUMENTS

| | | |
|---|---|---|
| 2005/0147151 A1 | 7/2005 | Nakazawa et al. |
| 2005/0154327 A1 | 7/2005 | Nakazawa |
| 2005/0163189 A1 | 7/2005 | Nakazawa et al. |
| 2005/0226310 A1 | 10/2005 | Nakazawa et al. |
| 2006/0264767 A1* | 11/2006 | Shennib ............ A61B 5/25 600/509 |
| 2012/0003933 A1* | 1/2012 | Baker ............ A61B 5/14542 455/41.2 |
| 2014/0246924 A1 | 9/2014 | Proud |
| 2015/0313486 A1 | 11/2015 | Mestha et al. |
| 2016/0262619 A1 | 9/2016 | Marcus et al. |
| 2016/0338646 A1 | 11/2016 | Lee et al. |
| 2016/0338798 A1* | 11/2016 | Vora ............ A61B 90/98 |
| 2017/0258349 A1 | 9/2017 | Watanabe |
| 2017/0366921 A1* | 12/2017 | Pflugh ............ A61N 1/37254 |
| 2019/0329038 A1* | 10/2019 | Rhude ............ A61B 5/363 |

FOREIGN PATENT DOCUMENTS

| | | | |
|---|---|---|---|
| JP | 2001-198096 A | 7/2001 | |
| JP | 2001-212095 A | 8/2001 | |
| JP | 2003-270051 A | 9/2003 | |
| JP | 2010-197245 A | 9/2010 | |
| JP | 2016-047092 A | 4/2016 | |
| WO | WO-2012140559 A1 * | 10/2012 | ...... A61B 5/0402 |
| WO | WO-2016031179 A1 * | 3/2016 | ...... A61B 5/0022 |
| WO | 2016/145314 A1 | 9/2016 | |

OTHER PUBLICATIONS

International Search Report Issued in Patent Application No. PCT/JP2019/002282 dated Apr. 15, 2019.
Written Opinion Issued in Patent Application No. PCT/JP2019/002282 dated Apr. 15, 2019.
Japanese Office Action dated Feb. 14, 2023, issued in Japanese Patent Application No. 2018-189957.
Japanese Office Action dated Nov. 8, 2022 issued in Japanese Patent Application No. 2018-189957.

* cited by examiner

PORTABLE ELECTROCARDIOGRAPH AND ELECTROCARDIOGRAPHY SYSTEM

TECHNICAL FIELD

The presently disclosed subject matter relates to a portable electrocardiograph which is carried by a subject and records data corresponding to electrocardiograms of the subject. The presently disclosed subject matter also relates to an electrocardiography system including the portable electrocardiograph.

BACKGROUND ART

In order to detect arrhythmias, there are tests in which electrocardiograms of a subject are collected over a long period of time. Japanese Patent Publication No. H08-299293A discloses an example of an electrocardiograph used for such examinations. The electrocardiograph is provided with electrodes. During the examination period, an electrocardiogram is recorded under a condition that the electrodes are always in close contact with the skin of the subject.

The electrocardiograph described in Japanese Patent Publication No. H08-299293A is equipped with a battery that supplies electric power for usually recording an electrocardiogram. Batteries tend to be large and heavy in order to allow long-term measurements. Electrocardiographs equipped with such batteries also tend to be larger and heavier, so that prolonged wear thereof increases the burden on the subject.

SUMMARY OF INVENTION

The presently disclosed subject matter is intended to reduce the burden imposed on a subject carrying an electrocardiograph.

An illustrative aspect of the presently disclosed subject matter provides a portable electrocardiograph comprising:
 a recording section configured to record data corresponding to electrocardiogram of a subject;
 a detecting section configured to detect approach of a portable device having a function to perform short-range wireless communication; and
 a control section configured to start recording of the data in the recording section in a case where it is satisfied a start condition including a fact that the approach of the device is detected by the detecting section.

An illustrative aspect of the presently disclosed subject matter provides an electrocardiography system comprising:
 an electrocardiograph configured to be carried by a subject; and
 a portable device having a function to perform short-range wireless communication,
 wherein the electrocardiograph comprises:
 a recording section configured to record data corresponding to electrocardiogram of the subject;
 a detecting section configured to detect approach of the device; and
 a control section configured to start recording of the data in the recording section in a case where it is satisfied a start condition including a fact that the approach of the device is detected by the detecting section.

According to such a configuration, the electrocardiogram data is recorded only when the subject is aware of the abnormality and brings the portable device closer to the portable electrocardiograph, so that the battery to be installed in the portable electrocardiograph can be downsized or omitted. As a result, downsizing and weight reduction of the portable electrocardiograph are realized, so that the burden to be imposed to the subject due to the carriage of the portable electrocardiograph can be reduced.

In addition, since recording is started by bringing the portable device having the short-range wireless communicating function close to the portable electrocardiograph, it is possible to make noise such as electromyographic information harder to be mixed into the electrocardiograph data. In addition, since the recording can be started irrespective of the place while keeping the clothes on, it is easy to avoid a loss of the recording opportunity due to the delay of the initial operation. Furthermore, since the electrocardiogram data can be recorded through the electrode fixed to a predetermined body position of the subject, it is easy to maintain the accuracy of the acquired data. Accurate recording of electrocardiogram data over a longer period is therefore possible.

DESCRIPTION OF EMBODIMENTS

Examples of embodiments are described in detail below with reference to the accompanying drawings.

Figure 1:
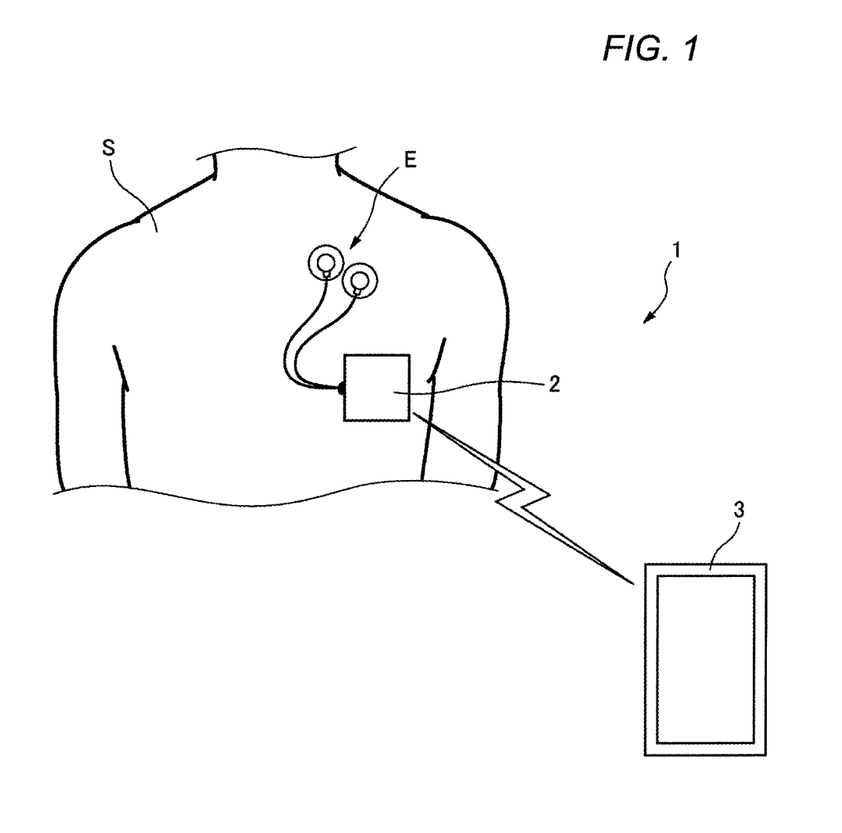
FIG. 1 illustrates a configuration of an electrocardiography system according to an embodiment.

As illustrated in FIG. 1, an electrocardiography system 1 according to an embodiment includes a portable electrocardiograph 2. The electrocardiograph 2 is carried by a subject S. In other words, the electrocardiograph 2 is configured so as to have such size and weight that the subject S is able to carry.

Figure 2:
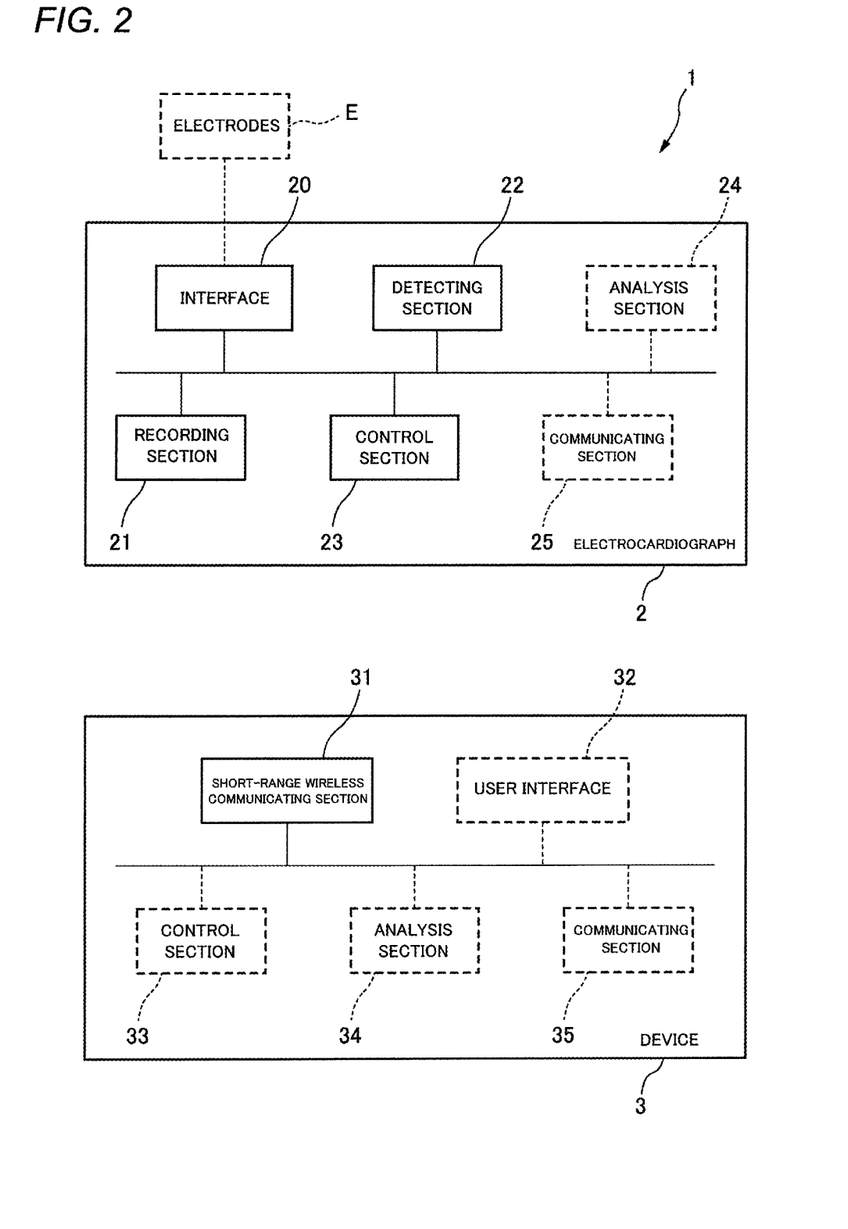
FIG. 2 illustrates a functional configuration of a portable electrocardiograph and a portable device in the electrocardiography system.

As illustrated in FIG. 1, a plurality of electrodes E are attached and fixed to the chest of the subject S. Each electrode E detects the biopotential of a body position on which the electrode E is attached. As illustrated in FIG. 2, the electrocardiograph 2 is provided with an interface 20. A signal corresponding to the biopotential detected through each electrode E is input to the interface 20. The interface 20 includes a circuit for converting the input signal into electrocardiogram data necessary for subsequent processing. Examples of the circuit include an A/D conversion circuit, a filter circuit, and the like. That is, the electrocardiogram data is digital data corresponding to the electrocardiogram of the subject S.

In the example illustrated in FIG. 1, a plurality of electrodes E are wired to the electrocardiograph 2. However, a signal corresponding to the biopotential detected through each electrode E may be input to the interface 20 via wireless communication. Alternatively, a configuration in which a plurality of electrodes E are built in the electrocardiograph 2 may be adopted. In this case, the electrocardiograph 2 is mounted and fixed on the chest of the subject S.

As illustrated in FIG. 2, the electrocardiograph 2 is provided with a recording section 21. The recording section 21 is configured to include a storage for recording electrocardiogram data. As the storage, a semiconductor memory, a hard disk drive, or the like can be exemplified.

As illustrated in FIG. 1, the electrocardiography system 1 includes a portable device 3 (hereinafter, simply referred to as a device 3). The device 3 can be carried by the subject S. In other words, the portable device 3 is configured so as to have such size and weight that the subject S is able to carry. The device 3 has a function to perform short-range wireless communication.

Specifically, as illustrated in FIG. 2, the device 3 is provided with a short-range wireless communicating section 31. The short-range wireless communicating section 31 can be configured by a communication interface conforming to standards such as RFID (Radio Frequency Identification), NFC (Near Field Communication), and Bluetooth (registered trademark). These standards are specified so that the wireless communication is not obstructed by ordinary clothing or the like.

As illustrated in FIG. 2, the electrocardiograph 2 is provided with a detecting section 22. The detecting section 22 is configured to be able to detect the approach of the device 3. Specifically, the detecting section 22 is configured to include a communication interface paired with the short-range wireless communicating section 31 of the device 3. The detecting section 22 detects the approach of the device 3 based on the fact that communication has been established with the communication interface of the short-range wireless communicating section 31.

Figure 3:
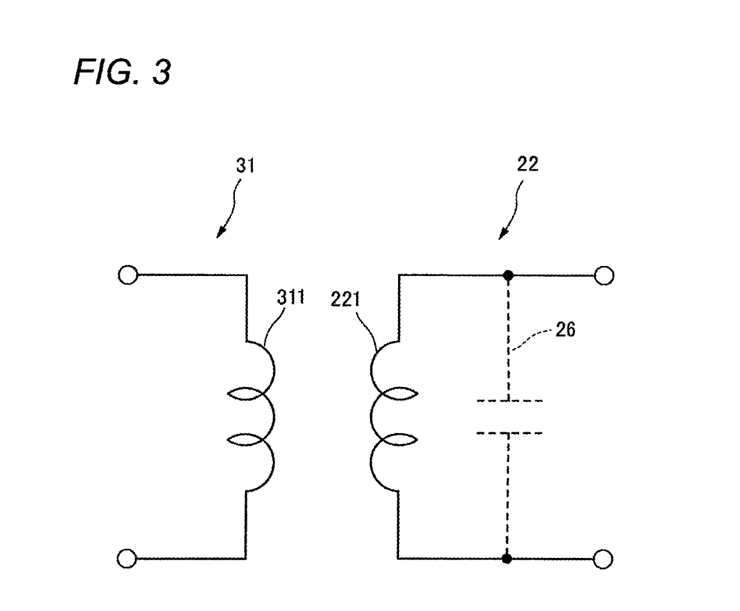
FIG. 3 illustrates the principle of contactless power delivery between the portable device and the portable electrocardiograph described above.

For example, as illustrated in FIG. 3, the short-range wireless communicating section 31 may be provided with a transmission coil 311. On the other hand, the detecting section 22 may be provided with a receiving coil 221. When a current is supplied to the transmission coil 311 by a power source (not shown) provided in the device 3, a magnetic flux is generated from the transmission coil 311. By bringing the device 3 closer to the electrocardiograph 2, a current flows through the receiving coil 221 due to the magnetic flux generated from the transmitting coil 311. The detecting section 22 detects the approach of the device 3 based on the fact that the induced current flows through the receiving coil 221.

As illustrated in FIG. 2, the electrocardiograph 2 is provided with a control section 23. The control section 23 is configured to start recording the electrocardiogram data in the recording section 21 in a case where a start condition is satisfied. The start condition includes the detection of the approach of the device 3 by the detecting section 22. The operation of the control section 23 and the recording of the electrocardiogram data by the recording section 21 are performed by the electric power supplied from the device 3 to the electrocardiograph 2 through the electromagnetic induction.

Next, with reference to FIG. 4, the electrocardiographic recording process performed with the electrocardiograph 2 and the device 3 configured as described above will be described in detail.

The electrocardiograph 2 is carried by the subject S in a state in which a plurality of electrodes E are attached and fixed to a predetermined body position. The subject S is instructed to bring the device 3 closer to the electrocardiograph 2 when the subject S is aware of an abnormality such as palpitation in daily life.

In the initial state, the electrocardiograph 2 is in a standby state. The control section 23 determines whether the start condition is satisfied (STEP1). That is, the control section 23 determines whether or not the approach of the device 3 is detected by the detecting section 22. At normal times, the subject S does not bring the device 3 closer to the electrocardiograph 2. Therefore, it is determined that the approach of the device 3 is not detected (N in STEP). Thus, the standby state of the electrocardiograph 2 is maintained.

When the subject S is aware of abnormalities such as palpitations, the subject S brings the device 3 closer to the electrocardiograph 2. Therefore, it is determined that the approach of the device 3 is detected (Y in STEP1). Therefore, the standby state of the electrocardiograph 2 is canceled, and the control section 23 starts recording the electrocardiogram data in the recording section 21 (STEP2). The power required for signal processing in the interface 20 and recording of electrocardiogram data in the recording section 21 is at least partially supplied from the device 3 through electromagnetic induction.

According to such a configuration, the electrocardiogram data is recorded only when the subject S is aware of the abnormality and brings the device 3 closer to the electrocardiograph 2, so that the battery to be installed in the electrocardiograph 2 can be downsized or omitted. As a result, downsizing and weight reduction of the electrocardiograph 2 are realized, so that the burden to be imposed to the subject S due to the carriage of the electrocardiograph 2 can be reduced.

In addition, since recording is started by bringing the device 3 having the short-range wireless communicating function close to the electrocardiograph 2, it is possible to make noise such as electromyographic information harder to be mixed into the electrocardiograph data. In addition, since the recording can be started irrespective of the place while keeping the clothes on, it is easy to avoid a loss of the recording opportunity due to the delay of the initial operation. Furthermore, since the electrocardiogram data can be recorded through the electrode E fixed to a predetermined body position of the subject S, it is easy to maintain the accuracy of the acquired data. Accurate recording of electrocardiogram data over a longer period is therefore possible.

In particular, since the electric power required for recording the electrocardiogram data is at least partially supplied from the device 3 through non-contact power supply such as electromagnetic induction, it is easy to downsize or omit the battery to be installed in the electrocardiograph 2.

In addition to the detection of the approach of the device 3 by the detecting section 22, another condition may be included in the start condition. For example, the start condition may include that the time during which the approach of the device 3 is detected by the detecting section 22 exceeds a predetermined value.

According to such a configuration, it is easy to avoid a situation in which the standby state of the electrocardiograph 2 is canceled by the fact that the subject S unintentionally brings the device 3 closer to the electrocardiograph 2. Therefore, the battery to be installed in the electrocardiograph 2 can be easily downsized or omitted. Further, the above advantage can be obtained by a simple processing performed with an internal timer.

Additionally or alternatively, as illustrated in FIG. 2, the device 3 may be provided with a user interface 32. Examples of the user interface 32 include a physical button, a lever, a touch-operable button displayed on a display device, and a voice recognition interface.

In this case, the start condition may include that a predetermined recording start operation has been performed on the user interface 32 of the device 3. Examples of the predetermined recording start operation include an operation of a physical button or a lever, a touch operation of a button displayed on a display device, and an input of sound associated with the start of recording.

The device 3 may be provided with a control section 33. When a predetermined recording start operation is performed on the user interface 32, the control section 33 generates a start instruction signal corresponding to the operation, and transmits the generated start instruction signal to the short-distance wireless communicating section 31. If communication is established between the detecting section 22 and the short-range wireless communicating section 31, a start instruction signal is received by the detecting section 22. The control section 23 of the electrocardiograph 2 determines that a predetermined recording start operation has been performed on the device 3 based on the fact that the start instruction signal has been received by the detecting section 22.

Even with such a configuration, it is easy to avoid a situation in which the standby state of the electrocardiograph 2 is canceled by the fact that the subject S unintentionally brings the device 3 closer to the electrocardiograph 2. Therefore, the battery to be installed in the electrocardiograph 2 can be easily downsized or omitted.

The control section 23 of the electrocardiograph 2 may be configured to stop recording the electrocardiogram data to the recording section 21 when a predetermined stop condition is satisfied.

Figure 4:
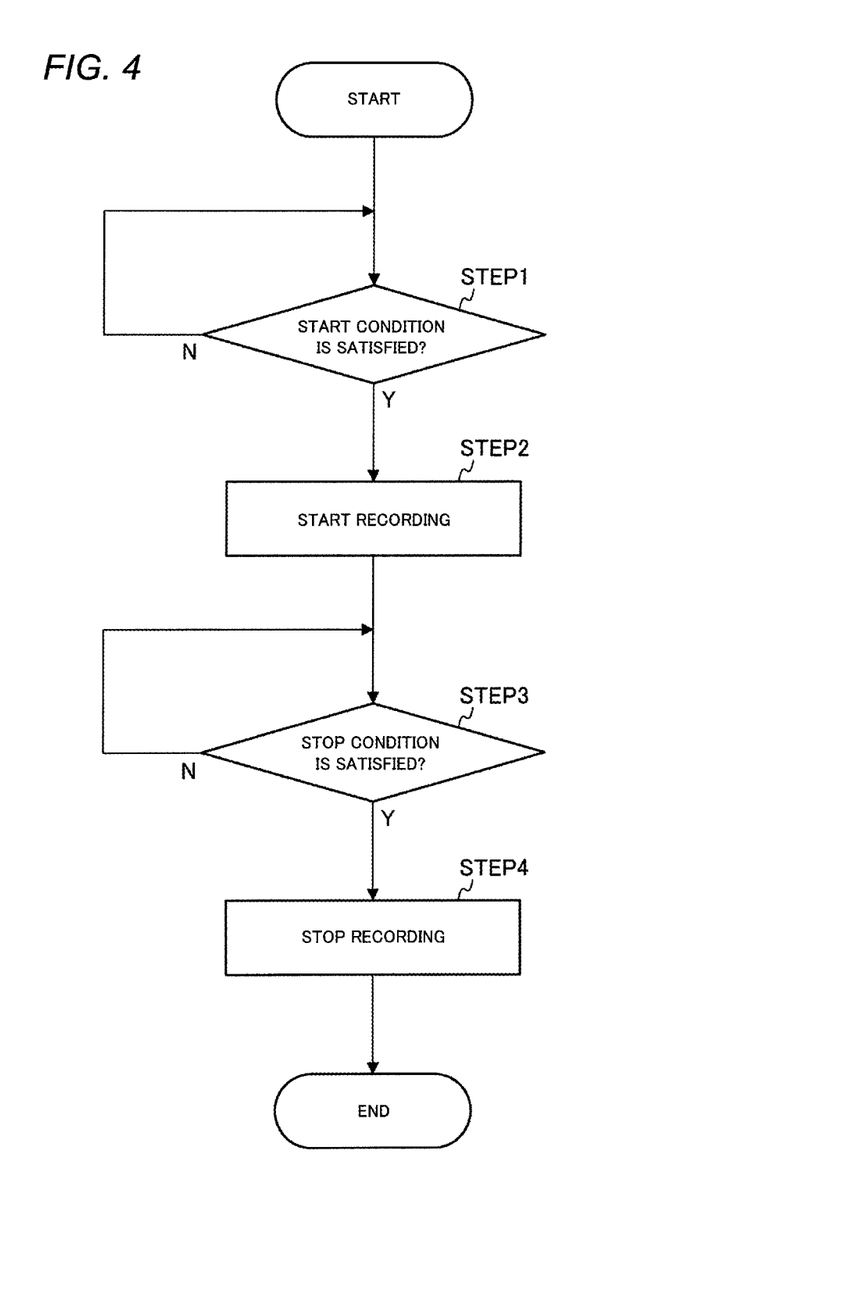
FIG. 4 illustrates the process performed by the portable electrocardiograph described above.

As illustrated in FIG. 4, while the electrocardiogram data is recorded in the recording section 21, the control section 23 determines whether the condition is satisfied (STEP3). If it is determined that the stopping condition is not satisfied (N in STEP3), recording of electrocardiogram data in the recording section 21 is continued.

When it is determined that the condition precedent has been satisfied (Y in STEP3), the control section 23 stops (STEP4) recording the electrocardiogram data in the recording section 21 and shifts the electrocardiograph 2 to the standby state.

According to such a configuration, the standby state of the electrocardiograph 2 can be canceled only during the period from the time when the start condition is satisfied to the time when the stop condition is satisfied. Therefore, the battery to be installed in the electrocardiograph 2 can be easily downsized or omitted.

The stop condition may include the elapse of a predetermined time period from the start of recording of the electrocardiogram data to the recording section 21. In this case, the control section 23 counts the elapsed time period from the start of recording with the internal timer. When the counted elapsed time period reaches a predetermined value, the control section 23 automatically stops recording the electrocardiogram data in the recording section 21.

According to such a configuration, with the aid of the simple automation processing performed with the internal timer, downsizing or omission of the battery to be installed in the electrocardiograph 2 can be realized.

Additionally or alternatively, the stop condition may include the fact that a predetermined recording stop operation has been performed on the user interface 32 of the device 3. As the predetermined recording stop operation, an operation of a physical button or a lever, a touch operation of a button displayed on a display device, an input of sound associated with the stop of recording, and the like can be exemplified.

In this case, when a predetermined recording stop operation is performed on the user interface 32, the control section 33 generates a stop instruction signal corresponding to the operation, and transmits the generated stop instruction signal to the short-distance wireless communicating section 31. If communication is established between the detecting section 22 and the short-range wireless communicating section 31, a stop instruction signal is received by the detecting section 22. The control section 23 of the electrocardiograph 2 determines that a predetermined recording stop operation has been performed on the device 3 based on the fact that the stop instruction signal has been received by the detecting section 22.

According to such a configuration, since the recording of the electrocardiogram by the electrocardiograph 2 can be stopped based on the discretion of the subject S, it is facilitated to downsize or omit the battery to be installed.

Additionally or alternatively, as illustrated in FIG. 2, the electrocardiograph 2 may be provided with an analysis section 24. The analysis section 24 is configured to analyze the electrocardiogram data recorded in the recording section 21 and detect the presence of an arrhythmia. Since the processing per se for detecting the presence or absence of the arrhythmia based on the acquired electrocardiogram data is known, detailed descriptions thereof will be omitted.

In this case, the stop condition may include the elapse of a predetermined time period from the time when the disappearance of the arrhythmia is detected by the analysis section 24. The control section 23 counts the elapsed time period from the detection of the disappearance of the arrhythmia with the internal timer. When the counted elapsed time period reaches a predetermined value, the control section 23 automatically stops recording the electrocardiogram data in the recording section 21.

According to such a configuration, it is possible to realize downsizing or omission of the battery to be installed in the electrocardiograph 2 while ensuring acquisition of the electrocardiogram data relating to the arrhythmia.

Figure 5:
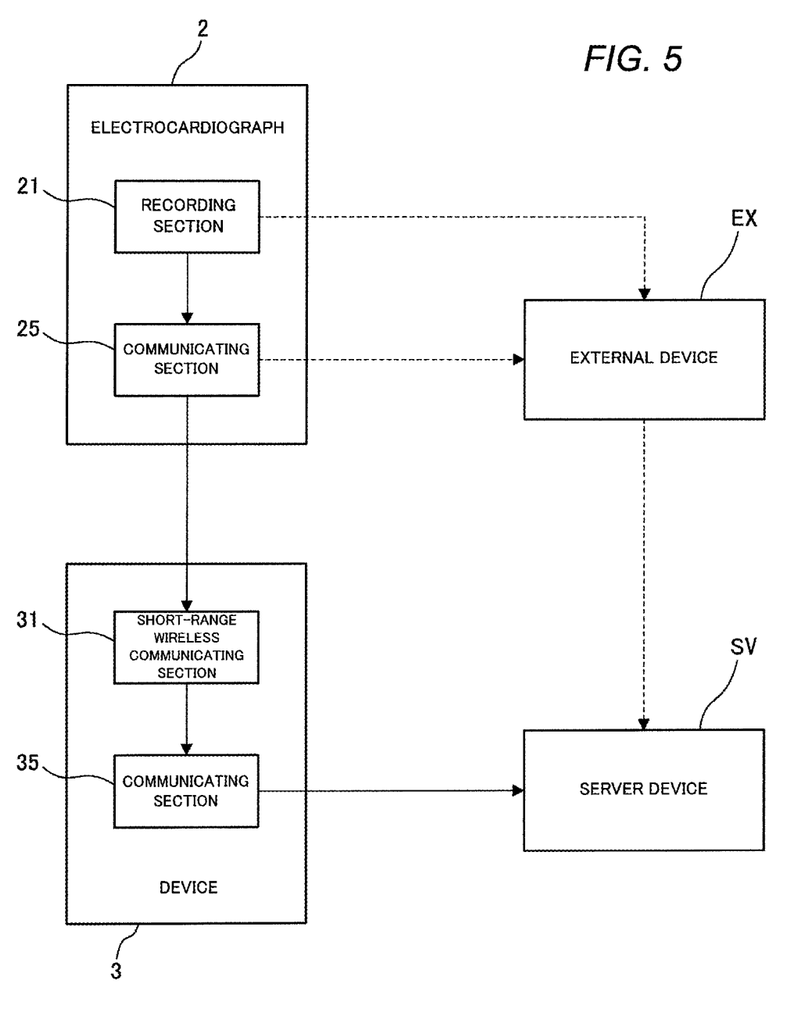
FIG. 5 illustrates the flow of electrocardiogram data in the electrocardiography system described above.

As illustrated in FIG. 2, the electrocardiograph 2 may be provided with a communicating section 25. As illustrated in FIG. 5, the communicating section 25 is configured to wirelessly transmit the electrocardiogram data recorded in the recording section 21 to the device 3. The communicating section 25 may be configured as a communication interface capable of establishing wireless communication with the short-range wireless communicating section 31 of the device 3. That is, the communication interface constituting the detecting section 22 can be at least partially shared.

According to such a configuration, it is possible to simplify the configuration required for holding and processing the electrocardiogram data in the electrocardiograph 2. As a result, it is possible to further suppress the increase in size and weight of the electrocardiograph 2, and further reduce the burden on the subject S due to the long-term examination.

When the electrocardiogram data is transmitted to the device 3 by the communicating section 25, the device 3 may be provided with an analysis section 34 as illustrated in FIG. 2. The analysis section 34 is configured to analyze the electrocardiogram data transmitted by the communicating section 25 and detect the presence of an arrhythmia. Since the processing per se for detecting the presence or absence of the arrhythmia based on the acquired electrocardiogram data is known, detailed descriptions thereof will be omitted.

In this case, the stop condition may include the elapse of a predetermined time period from the time when the disappearance of the arrhythmia is detected by the analysis section 34. The control section 33 counts the elapsed time period from the detection of the disappearance of the arrhythmia with the internal timer. When the counted elapsed time period reaches a predetermined value, the control section 33 generates a stop instruction signal, and causes the short-distance wireless communicating section 31 to transmit the generated stop instruction signal. If communication is established between the communicating section 25 and the short-range wireless communicating section 31, a stop instruction signal is received by the communicating section 25. The control section 23 of the electrocardiograph 2 determines that the stop condition is satisfied based on the fact that the stop instruction signal is received by the communicating section 25.

According to such a configuration, the analysis section 24 can be omitted from the electrocardiograph 2. As a result, it is possible to further suppress the increase in size and weight of the electrocardiograph 2 while ensuring acquisition of electrocardiogram data relating to arrhythmias, so that the burden on the subject S due to the long-term examination can be further reduced.

As illustrated in FIG. 2, the device 3 may be provided with a communicating section 35. As illustrated in FIG. 5, the communicating section 35 may be configured to transfer the electrocardiogram data received from the electrocardiograph 2 to a predetermined server device SV via a wireless communication network. The wireless communication network may include a wireless LAN, a cellular telephone communication network, the Internet, and the like. Examples of the device 3 provided with the communicating section 35 include a smart phone, a tablet terminal, and a notebook personal computer. The server device SV may be a general-purpose mail server device or a dedicated web server device.

The data transmitted to the server device SV may take various forms. The data may be binary data, which is electrocardiogram data itself, or may be data in a file format provided as an image or report processed to include electrocardiogram data.

According to such a configuration, even in a remote place, it is easy to confirm or share the electrocardiogram data recorded based on the awareness of the subject S. When the server device SV is a general-purpose mail server device, electrocardiogram data is sent to a mail address registered in the mail server device. By opening the mail, it is possible to confirm and diagnose electrocardiogram data in a remote place. When the server device SV is a dedicated web server device, a plurality of medical workers can share, irrespective of places, electrocardiogram data through a dedicated web page.

At least some of the functions of at least one of the interface 20, the detecting section 22, and the control section 23 in the electrocardiograph 2 may be realized by at least one processor and at least one memory. Examples of the processor may include a CPU and an MPU. A processor may be provided with a plurality of processor cores. Examples of the memory may include ROM and RAM. A program for realizing the above functions can be stored in the ROM. The processor may designate at least a part of a program stored in the ROM and load the program on the RAM in order to realize the above-described functions in cooperation with the RAM.

At least a part of the functions of the detecting section 22 and the control section 23 in the electrocardiograph 2 may be realized by at least one hardware resource such as an integrated circuit such as an ASIC or an FPGA, that is different from the above-described processor and memory.

At least a part of the functions of at least one of the control section 33 and the analysis section 34 in the device 3 can be realized by at least one processor and at least one memory. Examples of the processor may include a CPU and an MPU. A processor may be provided with a plurality of processor cores. Examples of the memory may include ROM and RAM. A program for realizing the above functions can be stored in the ROM. The processor may designate at least a part of a program stored in the ROM and load the program on the RAM in order to realize the above-described functions in cooperation with the RAM.

At least a part of the functions of the control section 33 and the analysis section 34 in the electrocardiograph 2 may be realized by at least one hardware resource such as an integrated circuit such as an ASIC or an FPGA, that is different from the above-described processor and memory.

The above embodiment is merely exemplary to facilitate understanding of the presently disclosed subject matter. The configuration according to the above embodiment can be appropriately modified or improved without departing from the fundamental concept of the presently disclosed subject matter.

As illustrated in FIG. 3, the electrocardiograph 2 may be provided with a condenser 26. The condenser 26 temporarily stores the electric power received from the device 3 via the contactless power supply. The condenser 26 is connected in parallel with the receiving coil 221, for example. The electric power temporarily stored in the condenser 26 can be supplied to at least the recording section 21 even after the non-contact power supply from the device 3 is canceled.

According to such a configuration, it is possible to shorten the time required to maintain the state in which the device 3 is brought close to the electrocardiograph 2 for contactless power supply while eliminating the need to install the battery in the electrocardiograph 2. Therefore, the burden on the subject S can be reduced.

As illustrated in FIG. 5, the communicating section 25 may be configured to wirelessly transmit the electrocardiogram data recorded in the recording section 21 to a dedicated external device EX. In this case, the communicating section 25 is configured as a communication interface capable of establishing wireless communication with the external device EX of the transmission destination. The electrocardiogram data transmitted to the external device EX may be subjected to storage processing, analysis processing, edit processing, and the like. The data processed by the external device may be transmitted to a predetermined server device SV via a communication network.

In a case where the electrocardiograph 2 is not provided with the communicating section 25, as illustrated in FIG. 5, the electrocardiogram data recorded in the recording section 21 can be directly read out by the dedicated external device EX. The data may be read out via a wired connection, or may be transferred by transferring the portable storage medium on which the electrocardiogram data is recorded from the electrocardiograph 2 to the external device EX. The electrocardiogram data transferred to the external device EX may be subjected to storage processing, analysis processing, edit processing, and the like. The data processed by the external device may be transmitted to a predetermined server device SV via a communication network.

In the above embodiment, signals from the plurality of electrodes E are input to the interface 20 of the electrocardiograph 2. However, a configuration in which a signal from a single electrode E is input to the interface 20 may also be employed.

When the electrocardiograph 2 is equipped with a battery for supplying electric power necessary for recording electrocardiograph data, it is not necessarily required to provide a power source on the side of the device 3 in order to perform the short-range wireless communication described above. The device 3 may be an IC card having excellent portability. In this case, it is possible to further reduce the burden on the subject S who is engaged in a long-term examination.

The present application is based on Japanese Patent Application No. 2018-017136 filed on Feb. 2, 2018 and Japanese Patent Application No. 2018-189957 filed on Oct. 5, 2018, the entire contents of which are hereby incorporated by reference.

The invention claimed is:

1. A portable electrocardiograph comprising:
a recording section configured to record data corresponding to electrocardiogram of a subject;
a detecting section configured to detect approach of a portable device having a function to perform short-range wireless communication; and
a control section configured to start recording of the data in the recording section when start conditions are satisfied, the start conditions comprising a first condition that the approach of the device is detected by the detecting section and a second condition that an input operation from a user is performed on the device.

2. The portable electrocardiograph according to claim 1, wherein the start conditions further comprise a third condition that a time period in which the approach of the device is detected exceeds a predetermined value.

3. The portable electrocardiograph according to claim 1, wherein the control section is configured to stop the recording of the data in the recording section when a predetermined stop condition is satisfied.

4. The portable electrocardiograph according to claim 3, wherein the stop condition is a condition that a predetermined time period elapses from time when the recording of the data in the recording section is started.

5. The portable electrocardiograph according to claim 3, comprising:
an analysis section configured to analyze the data to detect presence of an arrhythmia,
wherein the stop condition is a condition that a predetermined time period elapses from time when disappearance of the arrhythmia is detected by the analysis section.

6. The portable electrocardiograph according to claim 1, comprising:
a communicating section configured to wirelessly transmit data recorded in the recording section.

7. The portable electrocardiograph according to claim 1, wherein power to be supplied to at least the recording section is at least partially received from the device via non-contact power supply.

8. The portable electrocardiograph according to claim 7, comprising:
a condenser configured to temporarily store power received from the device.

9. An electrocardiography system comprising:
an electrocardiograph configured to be carried by a subject; and
a portable device having a function to perform short-range wireless communication, wherein the electrocardiograph comprises:
a recording section configured to record data corresponding to electrocardiogram of the subject;
a detecting section configured to detect approach of the device; and
a control section configured to start recording of the data in the recording section when start conditions are satisfied, the start conditions comprising a first condition that the approach of the device is detected by the detecting section and a second condition that an input operation from a user is performed on the device.

10. The electrocardiography system according to claim 9, wherein the control section is configured to stop the recording of the data in the recording section in a case where a predetermined stop condition is satisfied.

11. The electrocardiography system according to claim 10, wherein the stop condition is a condition that a predetermined operation for stopping the recording of the data is performed with respect to the device.

12. The electrocardiography system according to claim 10,
wherein the electrocardiograph comprises a communicating section configured to wirelessly transmit data recorded in the recording section;
wherein the device comprises an analysis section configured to analyze the data to detect presence of an arrhythmia,
wherein the stop condition is a condition that a predetermined time period elapses from time when disappearance of the arrhythmia is detected by the analysis section.

13. The electrocardiography system according to claim 9,
wherein the electrocardiograph comprises a communicating section configured to wirelessly transmit data recorded in the recording section;
wherein the device comprises a communicating section configured to transfer the data received from the electrocardiograph to a predetermined server device.

14. The electrocardiography system according to claim 9, wherein the device is configured to at least partially supply power to be supplied to at least the recording section in a non-contact manner.

15. The electrocardiography system according to claim 14, wherein the electrocardiograph comprises a condenser configured to temporarily store power received from the device.

* * * * *